(12) United States Patent
Danielmeier et al.

(10) Patent No.: US 6,395,925 B1
(45) Date of Patent: May 28, 2002

(54) PROCESS FOR PURIFYING ORGANIC ISOCYANATES, THE ORGANIC ISOCYANATES SO PURIFIED AND THEIR USE

(75) Inventors: Karsten Danielmeier, Bethel Park, PA (US); Dieter Mager, Leverkusen; Reinhard Halpaap, Odenthal, both of (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 09/569,480

(22) Filed: May 11, 2000

(30) Foreign Application Priority Data

May 17, 1999 (DE) .......................... 199 22 572

(51) Int. Cl.$^7$ ............................................. C07C 251/00
(52) U.S. Cl. ........................................ 560/352; 560/330
(58) Field of Search ................................ 560/352, 330

(56) References Cited

U.S. PATENT DOCUMENTS

| | | | |
|---|---|---|---|
| 3,219,678 A | 11/1965 | Kober et al. ................. | 260/453 |
| 3,264,336 A | 8/1966 | Powers ....................... | 260/453 |
| 3,274,225 A | 9/1966 | Saunders .................... | 260/453 |
| 3,373,182 A | 3/1968 | Powers ....................... | 260/453 |
| 3,458,558 A | 7/1969 | Cheng ......................... | 260/453 |
| 3,759,971 A | 9/1973 | Cuscurida et al. ..... | 260/453 SP |
| 3,793,362 A | 2/1974 | Kolakowski et al. .. | 260/453 SP |
| 3,799,963 A | 3/1974 | Adams .................. | 260/453 SP |
| 3,840,578 A | 10/1974 | Hennig ...................... | 260/453 |
| 3,853,936 A | 12/1974 | Van Winkle ........... | 260/453 SP |
| 3,857,871 A | 12/1974 | Hatfield, Jr. et al. ... | 260/453 SP |
| 4,094,894 A | 6/1978 | Blackwell .............. | 260/453 SP |
| 4,294,666 A | 10/1981 | Astheimer et al. ............ | 203/72 |
| 4,386,033 A | * 5/1983 | König et al. ................ | 260/453 |
| 5,386,054 A | 1/1995 | Scholl et al. ............... | 560/352 |

FOREIGN PATENT DOCUMENTS

| | | |
|---|---|---|
| DE | 1138040 | 10/1962 |
| DE | 1950101 | 4/1971 |
| DE | 271820 | 9/1989 |
| DE | 285593 | 12/1990 |
| DE | 288594 | 4/1991 |
| DE | 288595 | 4/1991 |
| DE | 288596 | 4/1991 |
| DE | 288597 | 4/1991 |
| DE | 288598 | 4/1991 |
| DE | 288599 | 4/1991 |
| GB | 1034357 | 6/1966 |
| GB | 1080717 | 8/1967 |
| GB | 1111581 | 5/1968 |
| GB | 1112450 | 5/1968 |
| GB | 1186896 | 4/1970 |
| GB | 1229181 | 4/1971 |
| GB | 1347647 | 2/1974 |
| GB | 1362708 | 8/1974 |
| GB | 1384065 | 2/1975 |
| GB | 1458747 | 12/1976 |
| GB | 1459691 | 12/1976 |
| GB | 1517162 | 7/1978 |
| JP | 67004137 | 2/1967 |
| JP | 70010329 | 12/1970 |
| JP | 59088452 | 5/1984 |
| JP | 59108753 | 6/1984 |
| JP | 59172450 | 9/1984 |
| JP | 61161250 | 7/1986 |
| JP | 5058982 | 3/1993 |
| JP | 5163231 | 6/1993 |
| JP | 6345707 | 12/1994 |
| JP | 7278088 | 10/1995 |
| JP | 9323968 | 12/1997 |
| SU | 806677 | 5/1982 |
| ZA | 8100606 | 7/1982 |

\* cited by examiner

Primary Examiner—Paul J. Killos
Assistant Examiner—Taylor V. Oh
(74) Attorney, Agent, or Firm—Joseph C. Gil; Lyndanne M. Whalen

(57) ABSTRACT

The invention provides a new process for purifying organic isocyanates or isocyanate mixtures by mixing the isocyanates or isocyanate mixtures to be purified with at least one alcohol and/or thiol or a mixture of alcohols and/or thiols, heating the resultant mixture and simultaneously or subsequently degassing the mixture and/or working up the mixture by distillation and/or extraction.

10 Claims, No Drawings

US 6,395,925 B1

PROCESS FOR PURIFYING ORGANIC ISOCYANATES, THE ORGANIC ISOCYANATES SO PURIFIED AND THEIR USE

BACKGROUND OF THE INVENTION

The present invention provides a new process for purifying one or more organic isocyanates or isocyanate mixtures. In this process, the isocyanate material to be purified is combined with one or more alcohols and/or thiols or mixtures of alcohols and/or thiols, the resultant mixture is heated and, optionally, simultaneously with or subsequent to being heated, degassed and/or worked up by distillation and/or extraction.

Impurities of varying types and amounts are generally present in organic isocyanates due to the method used for their preparation. These impurities are the cause of variable activity. Variable activity adversely affects the reproducibility of product properties and thus the economic viability of using the isocyanate having variable activity. Both aromatic isocyanates (for example the well-known phosgenation products of aniline/formaldehyde condensation and 2,4- and 2,6-diisocyanatotoluene) and aliphatic isocyanates (such as isophorone diisocyanate) contain a whole range of impurities of this type. These impurities are mainly chlorine-containing compounds which cause variations in the activity if the chlorine is "highly mobile" (i.e., so-called "hydrolyzable") chlorine. Some of these compounds have been shown to be relatively stable and they remain in the isocyanate even after distillation. They also exert a harmful effect on the stability of an isocyanate as well as on its activity. A more uniform, smaller proportion of these contaminants, resulting in activity standardization and simpler subsequent processing of isocyanates is therefore of both technical and economic importance.

There have been many attempts to find opportunities for removing the chlorine-containing compounds from isocyanates. Additives based on metals or alkali metals such as metal oxides, metal cyanamides, metal hydrides, metal fatty acid esters in the presence of sterically hindered phenols, metal naphthenates, metal silicates, alkali metal carbonates and organometallic compounds are described in JP 4 501 032 9 B; JP 4 200 413 7 B; JP 5 908 845 2 A; JP 5 910 875 3 A; JP 5 917 245 0 A; U.S. Pat. No. 3,373,182; GB-A 1 111 581; U.S. Pat. No. 3,759,971; U.S. Pat. No. 4,094,894; ZA 8 100 606; DE-A 11 38 040; DE-A 12 86 025; U.S. Pat. No. 3,458,558; U.S. Pat. No. 3,264,336; SU 8 066 77 and DE-A 22 10 607. In each of the processes disclosed in the patents and published applications mentioned above, a number of engineering difficulties which relate to isolation of the metal-containing additives or the restricted use of metal-containing isocyanates and/or distillation residues are encountered.

Similar difficulties are encountered when using additives such as the imidazole described in GB-A 1 347 647 and JP 0 505 898 2 A; the sulfonic acids and their esters described in GB-A 1 458 747; the diethyl sulfate described in GB 1 459 691 and the sulfuric acid also described there; the trialkyl phosphate described in DD 288 596; and the use of other additives such as epoxy compounds (DE-A 22 49 375; JP 0 932 396 8 A2), tetra-substituted ureas (DD 288 598), formic or acetic acid or their derivatives (U.S. Pat. No. 3,799,963) or the compounds which contain trimethylsilyl groups described in EP-A 524 507.

Some compounds with at least one Zerewitinoff-active NH group, such as urea (DD 285 594), biurets (DD 288 597), caprolactam (DD 285 593), ammonium salts (DD 288 594), carbodiimides (DD 288 599), primary and secondary amine salts (DD 288 593), tertiary alcohols and tertiary alkyl carbamates (DD 288 595) are recommended in the prior art for purifying isocyanates. Here again, isolation of the additives or the restricted use of additive-containing isocyanates and/or distillation residues, and in particular the sometimes large decrease in NCO index and the increase in viscosity, which can be attributed to the production of biurets when using tertiary alcohols, are disadvantages. The latter also applies to the use of water for purifying isocyanates (DE-A 12 40 849).

From publications JP 6 116 125 0 A; JP 0 516 323 1 A; DE-A 19 50 101; DE-A 19 38 384; DE-A 25 32 722; DE-A 26 31 168; U.S. Pat. No. 3,853,936; FR-A 1 555 517; DE-A 29 33 601; and U.S. Pat. No. 3,549,504, it is known that isocyanates can be purified by specific distillation and crystallization techniques.

It is also known that heating isocyanates, particularly when simultaneously stripping with an inert gas, or heating in an inert solvent under pressure with simultaneous removal by suction of the volatile compounds, reduces the concentration of readily decomposable chlorine compounds. (See, e.g., DE-A 12 70 036; DD 271 820; U.S. Pat. No. 3,219,678; GB-A 1 080 717; DE-A 22 37 552; U.S. Pat. No. 3,857,871; U.S. Pat. No. 1,458,223; JP 0 727 808 8 A2; JP 0 634 570 7 A2; and GB 1 384 065.) It is mainly the concentration of readily decomposable chlorine compounds that can be determined analytically as acidity which is decreased, whereas short-term heating may suppress the formation of sediments (U.S. Pat. No. 3,274,225).

SUMMARY OF THE INVENTION

It is an object of the present invention to provide a new process for purifying organic isocyanates which effectively removes impurities without creating the engineering difficulties experienced with prior art processes.

This and other objects which will be apparent to those skilled in the art are achieved by combining the isocyanate to be purified with an additive corresponding to a specified formula, heating the additive-containing isocyanate for at least 5 minutes at a temperature of from about 100 to about 250° C., and at the same time or subsequently the isocyanate being treated is stripped with an inert gas and/or is worked up by distillation and/or extraction.

DETAILED DESCRIPTION OF THE PRESENT INVENTION

The present invention relates to a process in which a small amount of at least one compound corresponding to Formula (I) described in more detail below is added to the organic isocyanate being treated, the isocyanate containing the compound corresponding to Formula (I) is then heated for a certain time, if required under elevated or reduced pressure, and at the same time or subsequently the isocyanate being treated is stripped with an inert gas and/or is purified by a single distillation and/or extraction procedure.

In the process for purifying organic isocyanates or isocyanate mixtures of the present invention, the organic isocyanate(s) or isocyanate mixture(s) is heated with a total of from about 0.01 to about 10 wt. %, based on the weight of organic isocyanate or isocyanate mixture, of at least one compound having a structure corresponding to Formula (I) or mixtures of compounds corresponding to Formula (I) below:

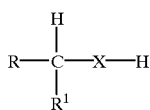

(I)

in which

X represents O or S and

R and R¹, independently represent H, or a $C_1$–$C_{36}$-alkyl, $C_6$–$C_{36}$-aryl, $C_3$–$C_{36}$-cycloalkyl or $C_7$–$C_{36}$-aralkyl group, or the groups R and R¹ may be linked via a ring system, or a primary X—H group, or a secondary X—H group, R and R¹ may also contain any of the previously specified groups which may further contain functional groups that do not react with an isocyanate group The isocyanate containing the compound corresponding to Formula (I) is heated for at least 5 min. at 100 to 250° C., with or without a solvent that is not reactive towards isocyanate groups, under elevated or reduced pressure, if necessary, and at the same time or subsequently is stripped with an inert gas and/or is worked up by distillation and/or extraction.

The organic isocyanates which may be purified by the process of the present invention are suitable as starting compounds for preparing polyurethane plastics by the isocyanate/polyaddition process, in particular when preparing polyisocyanates which are used as hardeners for surface coatings.

The starting materials for the process of the present invention include any organic isocyanate. Examples of suitable isocyanates include:

a) mono-isocyanates with aliphatically, cycloaliphatically, araliphatically or aromatically bonded isocyanate groups (e.g. butyl isocyanate, cyclohexyl isocyanate, phenyl isocyanate) or any mixture of such mono-isocyanates;

b) diisocyanates or higher-functional isocyanates with molecular weights in the range of from about 140 to about 400 with aliphatically, cycloatiphatically, araliphatically and/or aromatically bonded isocyanate groups such as 1,4-diisocyanatobutane, 1,6-diisocyanatohexane (HDI), 2-methyl-1,5-diisocyantopentane, 1,5-diisocyanato-2,2-dimethyl-pentane, 2,2,4- or 2,4,4-trimethyl-1,6-diisocyanatohexane, 1,10-diisocyanatodecane, 1,3- and 1,4-diisocyanatocyclohexane, 1,3- and 1,4-bis-(isocyanatomethyl)cyclohexane, 1-isocyanato-3,3,5-trimethyl-5-isocyanatocyclohexane (isophorone diisocyanate, IPDI), 4,4'-diisocyanatodicyclohexylmethane, 1-isocyanato-1-methyl-4(3)-isocyanatomethylcyclohexane (IMCI), bis-(isocyanatomethyl)-norbornane, 2-methylpentane-2,4-diisocyanate, 1,3- and 1,4-bis-(2-isocyanatoprop-2-yl)-benzene (TMXDI), 2,4- and 2,6-diisocyanatotoluene (TDI), 2,4'- and 4,4'-diisocyantodiphenylmethane, 1,5-diisocyanato-naphthalene, dipropylene glycol diisocyanate, 4-isocyanato-methyl-1,8-octane diisocyanate (nonane triisocyanate) and any mixture of such diisocyanates and/or higher functional isocyanates.

Diisocyanates and higher functional isocyanates are preferably used in the process of the present invention. Diisocyanates with aliphatically and cycloaliphatically bonded isocyanate groups are especially preferred.

The compounds corresponding to Formula (I) which may be used in the process of the present include monohydric or polyhydric, saturated or unsaturated, cyclic, linear or branched, primary and secondary alcohols, which preferably contain from 1 to 36, more preferably from 1 to 10, carbon atoms. Examples of suitable alcohols include: methanol, ethanol, n-propanol, isopropanol, n-butanol, isobutanol, n-pentanol, 2-hydroxypentane, 3-hydroxypentane, the isomeric primary and secondary methylbutyl alcohols, n-hexanol, n-heptanol, n-octanol, n-nonanol, 2-ethylhexanol, primary and secondary trimethylhexanols, cyclohexanol, benzyl alcohol, n-decanol, n-undecanol, n-dodecanol (lauryl alcohol), n-tetradecanol, n-pentadecanol, n-hexadecanol, n-heptadecanol, n-octadecanol (stearyl alcohol), 2,6,8-trimethylnonanol, 4-cyclohexyl-1-butanol, 2,4,6-trimethylbenzyl alcohol, branched and linear, primary and secondary alcohols and mixtures of these such as, for example, those sold by the Henkel Co. under the tradename Lorol, glycerol or other dihydric and higher-hydric alcohols with primary and/or secondary OH groups.

Compounds corresponding to Formula (I) which may be used in the process of the present invention also include monofunctional and polyfunctional, saturated or unsaturated, linear, branched or cyclic, primary and secondary thioalcohols which preferably contain from 1 to 36, most preferably about 10, carbon atoms and mixtures thereof.

The compounds with a structure corresponding to Formula (I) may, less preferably, contain other functional groups which are not reactive towards isocyanate groups such as esters, ethers or heteroatoms such as halogens (Cl, Br) or nitrogen in addition to the XH (X=O or S) group.

Obviously, in addition to mixtures of alcohols corresponding to Formula (I) and mixtures of thioalcohols corresponding to Formula (I), mixtures of alcohols and thioalcohols corresponding to Formula (I) may also be used in the process of the present invention. Solutions of compounds corresponding to Formula (I) or solutions of mixtures of compounds corresponding to Formula (I) in inert solvents (i.e., solvents which do not react with isocyanate groups) may also be used but use of such solutions is not preferred.

Aliphatic, primary $C_1$–$C_{10}$-monoalcohols or mixtures of aliphatic $C_1$–$C_{10}$-monoalcohols are preferably used in the process of the present invention. The use of n-butanol is particularly preferred.

The process of the present invention may also be carried out with phenols.

In the process of the present invention, the mixture of organic isocyanate and the compound corresponding to Formula (I), or of isocyanate mixture and a compound corresponding to Formula (I), or the isocyanate and a mixture of compounds corresponding to Formula (I) or the isocyanate mixture and a mixture of compounds corresponding to Formula (I), is heated with an amount of the compound or mixture of compounds corresponding to Formula (I) of from about 0.01 to about 10 wt. %, preferably from about 0.05 to about 5 wt. %, most preferably from about 0.1 to 2.5 wt. %, based on the weight of isocyanate or isocyanate mixture. The mixture being heated may optionally include an inert solvent (i.e., a solvent which is not reactive towards isocyanate groups). The isocyanate being treated is heated for a period of at least 5 min, preferably at least 240 min. to a temperature of from about 100 to about 250°, preferably at least 150° C., most preferably higher than 180°. If required, the mixture may be heated at an elevated or reduced pressure. The isocyanate being heated may be stripped with an inert gas during the heating process or afterwards and/or worked up by distillation and/or extraction. Working up by distillation is understood to mean, in the case of using distillable starting isocyanates, the preparation of pure compounds by distillation, for example in a thin layer evaporator or across a distillation bridge.-

Obviously, instead of stripping with an inert gas, degassing under vacuum (for example 100 to 1 mbar) may equally preferably be performed.

The percentages by weight mentioned for the compounds corresponding to Formula (I), or mixtures thereof, used in the process of the present invention may vary, depending on the equivalent weight of the compound(s) corresponding to Formula (I).

The NCO/XH ratio (where X=O, S) does not fall below 10 to 1 in the process of the present invention.

The organic isocyanate(s) treated in accordance with the invention exhibit reduced variation in activity. This can be readily demonstrated by the reduced values for hydrolyzable chlorine which translate into improved activities for foaming ability or improved color stability.

The invention is further illustrated but is not intended to be limited by the following examples in which all parts and percentages are by weight, unless otherwise specified.

EXAMPLES

The HC values cited refer to the concentration of hydrolyzable chlorine. All percentage data is given with respect to weight.

Examples

The amount of compound specified in Tables 1, 2 and 3 was added to 100 g of the organic isocyanate indicated and the mixture was stirred under a gentle stream of inert gas for the stated time at the stated temperature (=conditioning). After cooling, products of the process of the present invention were obtained. These products may optionally be distilled for further purification.

The product obtained in Example 7 according to the invention (Table 2) was distilled across a distillation bridge (head temperature 96°C.; pressure: $1.5 \times 10^{-2}$ mbar). 99.8% purity (GC), pale-colored isophorone diisocyanate was obtained.

TABLE 1

| Organic isocyanate | Example 1* isophorone diisocyanate (IPDI) | Example 2 isophorone diisocyanate (IPDI) | Example 3 isophorone diisocyanate (IPDI) | Example 4 hexamethylene diisocyanate (HDI) | Example 5 isophorone diisocyanate (IPDI) | Example 6 isophorone diisocyanate (IPDI) |
|---|---|---|---|---|---|---|
| Alcohol used | — | methanol | decanol | 1-butanol | stearyl alcohol | isobutanol |
| Wt. % of alcohol | — | 0.4 | 2 | 1 | 3.6 | 1 |
| Temperature | 220° C. | 220° C. | 220° C. | 220° C. | 220° C. | 220° C. |
| Reaction time [h] | 6 | 6 | 6 | 6 | 6 | 6 |
| HC value before conditioning | 156 ppm | 156 ppm | 156 ppm | 48 ppm | 156 ppm | 156 ppm |
| HC value after conditioning | 67 ppm | 4 ppm | 16 ppm | 3 ppm | 6 ppm | 20 ppm |
| Viscosity before conditioning | <50 mPa · s | <50 mPa · s | <50 mPa · s | <50 mPa · s | <50 mPa · s | <50 mPa · s |
| Viscosity after conditioning | <50 mPa · s | <50 mPa · s | <50 mPa · s | <50 mPa · s | <50 mPa · s | <50 mPa · s |

*Comparative Example

TABLE 2

| Organic isocyanate | Example 7 isophorone diisocyanate (IPDI) | Example 8 isophorone diisocyanate (IPDI) | Example 9 triisocyanatononane (TIN) | Example 10 triisocyanatononane (TIN) | Example 11* triisocyanatononane (TIN) | Example 12 isophorone diisocyanate (IPDI) |
|---|---|---|---|---|---|---|
| Alcohol used | n-butanol | methanol | n-butanol | n-butanol | — | 2-butanol |
| Wt. % of alcohol | 1 | 1 | 2.4 | 4 | — | 1 |
| Temperature | 220° C. | 220° C. | 220° C. | 200° C. | 200° C. | 220° C. |
| Reaction time [h] | 6 | 6 | 6 | 6 | 6 | 6 |
| HC value before conditioning | 156 ppm | 156 ppm | 2300 ppm | 2300 ppm | 2300 ppm | 156 ppm |
| HC value after conditioning | 5 ppm | 3 ppm | 161 ppm | 122 ppm | 800 ppm | 79 ppm |
| Viscosity before conditioning | <50 mPa · s | <50 mPa · s | <50 mPa · s | <50 mPa · s | <50 mPa · s | <50 mPa · s |
| Viscosity after conditioning | <50 mPa · s | <50 mPa · s | <50 mPa · s | <50 mPa · s | <50 mPa · s | <50 mPa · s |

*Comparative Example

TABLE 3

| Organic isocyanate | Example 13* isophorone diisocyanate (IPDI) | Example 14 isophorone diisocyanate (IPDI) | Example 15 isophorone diisocyanate (IPDI) | Example 16* 4,4'-diisocyanato-diphenylmethane | Example 17 4,4'-diisocyanato-diphenylmethane |
|---|---|---|---|---|---|
| Alcohol used | tert.-butanol | glycerol | n-butanol | — | n-butanol |
| Wt. % of alcohol | 1 | 1 | 2 | — | 1 |
| Temperature | 220° C. | 200° C. | 220° C. | 220° C. | 220° C. |
| Reaction time [h] | 6 | 6 | 2 | 6 | 6 |
| HC value before conditioning | 156 ppm | 156 ppm | 156 ppm | 391 ppm | 391 ppm |
| HC value after conditioning | 10 ppm | 33 ppm | 11 ppm | 151 ppm | 5 ppm |
| Viscosity before conditioning | <50 mPa · s | <50 mPa · s | <50 mPa · s | <50 mPa · s | <50 mPa · s |
| Viscosity after conditioning | 1850 mPa · s | 75 mPa · s | <50 mPa · s | <50 mPa · s | <50 mPa · s |

*Comparative Example

Comparative Examples 1, 11 and 16 show that without the addition of a compound corresponding to Formula (I), insufficient purification of the isocyanate occurs, which is demonstrated by a relatively high HC value after conditioning. In contrast, very low HC values are achieved by adding even a small amount of a compound in accordance with Formula (I). (See Example 2.)

Comparative Example 13 shows an unacceptably large increase in viscosity when using tert.-butanol in accordance with DD 288 595. When a compound corresponding to Formula (I) was used, the viscosity remained substantially lower. (See Example 15)

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A process for purifying an organic isocyanate comprising a) adding a compound corresponding to Formula (I)

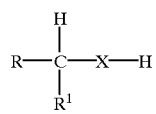

(I)

in which

X represents O or S and

R and $R^1$ independently, represent H, or a $C_1$–$C_{36}$-alkyl, $C_6$–$C_{36}$-aryl, $C_3$–$C_{36}$-cycloalkyl or $C_7$–$C_{36}$-aralkyl group, wherein the groups R and $R^1$ may be linked via a ring system and also either primary and secondary X—H groups or R and $R^1$ may also contain other functional groups which do not react with an isocyanate group, to the isocyanate to be purified in an amount of from about 0.01 to about 10 wt. %, based on the weight of the isocyanate, b) heating the product of a) for at least 5 minutes at a temperature of from about 100 to about 250° C., and c) conducting at least one step selected from (i) stripping the product of b) with an inert gas or (ii) purifying the product of b) by distillation or (iii) purifying the product of b) by extraction.

2. The process of claim 1 in which a solvent having no groups which are reactive with isocyanate groups is present during step b).

3. The process of claim 1 in which step b) is carried out without a solvent.

4. The process of claim 1 in which step b) is carried out at elevated pressure.

5. The process of claim 1 in which step b) is carried out at reduced pressure.

6. The process of claim 1 in which steps b) and c)(i) are conducted simultaneously.

7. The process of claim 1 in which step b) is substantially completed before step c) is carded out.

8. The process of claim 1 in which the compound corresponding to Formula (I) is a primary alcohol.

9. The process of claim 1 in which the compound corresponding to Formula (I) is n-butanol.

10. The process of claim 1 in which step c) comprises stripping the product of b) with an inert gas and purification of the product of b) by distillation.

* * * * *